United States Patent
Park et al.

(10) Patent No.: US 9,307,782 B2
(45) Date of Patent: Apr. 12, 2016

(54) MANNANASE PRODUCED FROM CELLULOSIMICROBIUM SP. STRAIN HY-13

(75) Inventors: Ho-Yong Park, Daejeon (KR); Kwang-Hee Son, Daejeon (KR); Do Young Kim, Daejeon (KR); Dong-Ha Shin, Daejeon (KR); Han-Young Cho, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 87 days.

(21) Appl. No.: 14/232,483

(22) PCT Filed: Dec. 28, 2011

(86) PCT No.: PCT/KR2011/010245
§ 371 (c)(1),
(2), (4) Date: Jan. 13, 2014

(87) PCT Pub. No.: WO2013/012141
PCT Pub. Date: Jan. 24, 2013

(65) Prior Publication Data
US 2014/0227762 A1    Aug. 14, 2014

(30) Foreign Application Priority Data

Jul. 15, 2011 (KR) .................. 10-2011-0070462

(51) Int. Cl.
| | |
|---|---|
| *C12N 9/24* | (2006.01) |
| *A23K 1/16* | (2006.01) |
| *A23K 1/165* | (2006.01) |
| *A23K 1/18* | (2006.01) |
| *A23L 1/305* | (2006.01) |

(52) U.S. Cl.
CPC ............... *A23L 1/3058* (2013.01); *A23K 1/165* (2013.01); *A23K 1/1653* (2013.01); *A23K 1/1656* (2013.01); *A23K 1/184* (2013.01); *A23K 1/1826* (2013.01); *C12N 9/2491* (2013.01); *C12Y 302/01025* (2013.01)

(58) Field of Classification Search
CPC ...................... C12N 9/2491; C12Y 302/01025
See application file for complete search history.

(56) References Cited

U.S. PATENT DOCUMENTS

2009/0325240 A1* 12/2009 Daniell ................ 435/101

FOREIGN PATENT DOCUMENTS

WO PCT/KR2011/010245    6/2012

OTHER PUBLICATIONS

Zahura, U.A., et al., 2010, "An endo-β-1,4-mannanase, AkMan, from the common sea hare Aplysia kurodai", Comparative Biochemistry and Physiology, Part B, vol. 157, pp. 137-143.*

(Continued)

*Primary Examiner* — Manjunath Rao
*Assistant Examiner* — William W Moore
(74) *Attorney, Agent, or Firm* — Licata & Tyrrell P.C.

(57) ABSTRACT

The present invention relates to a mannanase produced from *Celluosimicrobium* sp. strain HY-13 and more particularly to a highly active novel mannanase produced from *Cellulosimicrobium* sp. strain HY-13 as separated from an invertebrate. The mannanase produced from the said *Cellulosimicrobium* sp. strain HY-13 can be used in the decomposition of a mannan found in hemicellulose contained in grains and plants and in enhancing the utility value of a hydrolysate, which uses the decomposed mannan, for the transformation of biomass or as an animal feed material.

3 Claims, 6 Drawing Sheets

(56) References Cited

OTHER PUBLICATIONS

Kim, D.Y., et al., 2011, "A highly active endo-β-1,4-mannase produced by *Cellulosimicrobium* sp. strain HY-13 ,a hemicellulolytic bacterium in the gut of Eisenia fetida", Enzyme and Microbial Technology, vol. 48, pp. 365-370.*

Kim, D.Y., et al., 2011, "Cloning and characterization of a modular GH5 β-1,4-mannase with high specific activity from the fibrolytic bacterium *Cellulosimicrobium* sp. strain HY-13", Bioresource Technology, vol. 102, pp. 9185-9192.*

GenEmbl database Accession No./Locus JF519824, Sep. 3, 2011, *Cellulosimicrobium* sp. HY-13 beta-1,4,-mannanase (manH) gene, complete cds.*

UniProt/TrEMBL Accession No. B0ZSE6, Wang et al., 2008, "Cloning, DNA sequencing, and expression of the beta-1,4-mannanase gene from *Streptomyces* sp. s6-204", 531 amino acids.*

Kim et al. "Cloning and Characterization of a Modular GH5 beta-1,4-mannanase with High Specific Activity from the Fibrolytic Bacterium *Cellulosimicrobium* sp. Strain HY-13" Bioresearch Technology 2011 102:9185-9192.

Kim et al. "A Highly Active Endo-beta-1,4-mannanase Produced by *Cellulosimicrobium* sp. Strain HY-13, a Hemicellulolytic Bacterium in the Gut of *Eisenia fetida*" Enzyme and Microbial Technology 2011 48:365-370.

Kim et al. "Novel GH10 Xylanase, with a Fibronectin Type 3 Domain, from *Cellulosimicrobium* sp. Strain HY-13, a Bacterium in the Gut of *Eisenia fetida*" Applied and Environmental Microbiology 2009 75(22):7275-7279.

Shibasaki et al. "Isolation of Bacteria which Produce Yeast Cell Wall-Lytic Enzymes and Their Characterization" Biocontrol Science 2008 13(3): 91-96.

* cited by examiner

```
   1 ATGAGACGACTGTTCGCCATCGTCCTGGGCGCGGTGCTCGCCTTGCTCGCCGTGCCGGCG   60
     M   R   R   L   F   A   I   V   L   G   A   V   L   A   L   L   A   V   P   A
  61 CTCGCGCAGGGGGCGAGCGTCGCGAGCGACGGGTTCTCCGTCCAGGACGGGAGGATCTAC  120
     L   A   Q   G   A   S   V   A   S   D   G   F   S   V   Q   D   G   R   I   Y
 121 GACGCGAACGGCAACCGCTTCGTGCCGGTCGGCGTCAACCACGCGCACGCCTGGTACCCG  180
     D   A   N   G   N   R   F   V   P   V   G   V   N   H   A   H   A   W   Y   P
 181 TCGCAGACGCAGTCCTTCGCCGACATCCGCGCCGCCGGCGCGAACACCGTCCGCGTCGTG  240
     S   Q   T   Q   S   F   A   D   I   R   A   A   G   A   N   T   V   R   V   V
 241 CTGTCGGGCGGCCGGTACGGGACGAGCTCGGCGGCCGACGTGAGCGCCGTGGTCGAGCGC  300
     L   S   G   G   R   Y   G   T   S   S   A   A   D   V   S   A   V   V   E   R
 301 TGCAAGCAGAACCAGCTCGTGTGCATCCTCGAGAACCACGACACGACGGGCTACGGCGAG  360
     C   K   Q   N   Q   L   V   C   I   L   E   N   H   D   T   T   G   Y   G   E
 361 GACGGCAGCGCCCGGTCGCTCGCGAGCGCGGCGCAGTACTGGACCAGCATCGCGTCGGTC  420
     D   G   S   A   R   S   L   A   S   A   A   Q   Y   W   T   S   I   A   S   V
 421 CTGCGCGGCCAGGAGCGGTACGTGATGATCAACATCGGCAACGAGCCCTTCGGCAACTCC  480
     L   R   G   Q   E   R   Y   V   M   I   N   I   G   N   E   P   F   G   N   S
 481 GGCTTCCAGAGCTGGACGACGGACACGATCGCGGCGATCCGGACCCTGCGCGCGGCGGGC  540
     G   F   Q   S   W   T   T   D   T   I   A   A   I   R   T   L   R   A   A   G
 541 CTCGACCACACGCTCGTCGTGGACGCCCCGAACTGGGGACAGGACTGGTCGTTCACCATG  600
     L   D   H   T   L   V   V   D   A   P   N   W   G   Q   D   W   S   F   T   M
 601 CGCGACAACGCCCCGACGGTCGCGGCCGCGGACGGGAACGTGGTCTTCTCCGTCCACATG  660
     R   D   N   A   P   T   V   A   A   A   D   G   N   V   V   F   S   V   H   M
 661 TACGGCGTCTTCGACACCGGGGCGGAGGTGCGCGCGTACCTCGACTCCTTCACGAGCCGA  720
     Y   G   V   F   D   T   G   A   E   V   R   A   Y   L   D   S   F   T   S   R
 721 GGGCTGCCGATCATGGTCGGCGAGTTCGGTGACAACCACTCGGACGGGAACCCGGACGAG  780
     G   L   P   I   M   V   G   E   F   G   D   N   H   S   D   G   N   P   D   E
 781 GCCACGATCATGAGCTACACGCGGTCGCAGGGGATCGGGATGCTCGGCTGGTCGTGGTCC  840
     A   T   I   M   S   Y   T   R   S   Q   G   I   G   M   L   G   W   S   W   S
 841 GGCAACGGGGCGGCGTCGAGTACCTGGACATGGTGAACGGGTTCTCCGCGAGCTCGCTC  900
     G   N   G   G   V   E   Y   L   D   M   V   N   G   F   S   A   S   S   L
 901 ACGCCGTGGGGGCAGCGGTTCGTCCACGGCGCCGACGGGCTCAGGGCCCGCAACGCGCCC  960
     T   P   W   G   Q   R   F   V   H   G   A   D   G   L   R   A   R   N   A   P
 961 GCGGCCTCGGTGTACGGGGGCGACGGCGGCGATGGAGACGGCGGAGCCGGTACGGCACCC 1020
     A   A   S   V   Y   G   G   D   G   G   D   G   D   G   G   A   G   T   A   P
1021 AACGGGTACCCGTACTGCGCGAGCGCGTCGTCGGACCCGGACGGGGACGGGTGGGGCTGG 1080
     N   G   Y   P   Y   C   A   S   A   S   S   D   P   D   G   D   G   W   G   W
1081 GAGAGCAGCGCGTCGTGCGTGGTGCGCGGCTCCTCCGCGGACACGGGTTCCGGCGGTGGC 1140
     E   S   S   A   S   C   V   V   R   G   S   S   A   D   T   G   S   G   G
1141 TCCGGGAGCGGGAGCACGGCACCGAACGGGTACCCGTACTGCGCGAGCGCGTCGTCGGAC 1200
     S   G   S   G   S   T   A   P   N   G   Y   P   Y   C   A   S   A   S   S   D
1201 CCGGACGGGGACGGGTGGGGCTGGGAGAGCAGCGCCTCGTGCGTCGTGCGCGGCTCGTCC 1260
     P   D   G   D   G   W   G   W   E   S   S   A   S   C   V   V   R   G   S   S
1261 GCCGACCGCTGA                                                  1320
     A   D   R   *
```

Figure 3

```
Csp   1   ------------------------------------------MRRLFAIVLG
Msp   1   ------------------------------------------MRKRLSVAAV
Ssp  61   PPSPCQAPYRLGFLPGQRCRVVQEGAGRKVSSCPHHLRSNMAKQPRRLLRTVAGTAFAAA
Sco   1   ------------------------------------MRKPRSTLITTAGVAFAAV
Sli   1   ---------------MRDNVVRCMLARHRRRHMRKPRSTLITTAGVAFAAV

Csp  11   AVLALLAVPALAQGASVASLGFSVQDGRIYDANGNRFVPVGVNHAHAWYPSQTCSFADIR
Msp  11   ALLTVLAAVFAFGQPAHAAAGFTVANGKLYDANGNEFVMRGVNHAHTWYPCQTSSFANIK
Ssp 121   LGLLASVLGPSVGEAEAAFAGIRVHNGRVYEANGNEFVMRGANHAYAWYPSQTTSIADIA
Sco  20   LGLLFALAGPSAGRAEAAACGIHVSNGRVLEGNGSVFVMRGVNHAYTWYPDRTCSIADIA
Sli  37   LGLLFALAGPSAGRAEAAACGIHVSNGRVLEGNGSAFVMRGVNHAYTWYPDRTCSIADIA

Csp  71   AAGANTVRVVLSGG-RYGTSSAADVSAVVERCKQNQLVCTLEHDTTGYGEDGSARSLAS
Msp  71   ALGANTVRVVLASGDRWAKNDTADVANVISLCKANKTICVLEVHDTTGYGEQSGAITLDR
Ssp 181   AKGANTVRVVLGSGDRWTETSASEVSTIIGQCKANKVICVLEVHDTTGYGEDGAAATLDQ
Sco  80   AKGANTVRVVLSSGGRWTKTSASEVSALIGQCKANKVICVLEVHDTTGYGEDGAATSLDQ
Sli  97   AKGANTVRVVLSSG-RWTKTSASEVSALIGQCKANKVICVLEVHDTTGYGEDGAATSLDQ
                    *                    *
Csp 130   AASYWISLASVLFGQERYVMINIGNEPFGNSGFQSWTTDTIAAIRTLRAAGLDHTLVDA                    GH5 domain
Msp 131   AVDYWLSISSSALAGQEKYVIVNIGNEPYGNRGYGIWATDSANAIKRLRAAGLAHTIMIDA   164/250 (65%)
Ssp 241   AADYWIGVKSALEGQEDYVVVNIGNEPFGNSNYAAWTDATKSAIGKLRSAGLRHALMVDA   156/250 (62%)
Sco 140   AADYWVSVKSALEGQEDYVVVNIGNEPFGNTNYTAWTDATKSAIGKLRGAGLLHALMVDA   151/240 (62%)
Sli 157   AADYWVGVKSALEGQEDYVVVNIGNEPFGNTNYAAWTDATKSAIGKLRGAGLCHALMVDA   148/240 (61%)
                 →                        **
Csp 190   PNWGQDWSETMRDNAPTVAAADG--NVVFSVHMYGVEDTGAEVRAYLDSFTSRGLPIVVG
Msp 191   PNWGQDWSETMRDNAASVFAADPQKNTVFSVHMYGVEDTAAEISDYLSRFRTAKLPIVVG
Ssp 301   PNWGQDWSETMRNNAASVFASDPDRNTIFSIHMYGVYDTAAEVQDYLNHFVNNGLPLVVG
Sco 200   PNWGQDWSGTMRSNAASVFASDPDRNTVFSVHMYGVYDTAAEVRDYLNAFVSSGLPIVVG
Sli 217   PNWGQDWSCTMRSNAASVFASDPDRNTVFSIHMYGVYDTAAEVRDYLNAFVGNGLPIVVG
                                                  ←  **
Csp 248   EFGDNHSDGNPDEATIMSYTRSQGTGMLGWSWSGNGGGVEYLDMVNGFSASSSLTFWGQRF
Msp 251   EFGFLHSDGNPDEDTILSYTQANGIGYLGWSWSGNSGGVEYLDMVTNFNPAALLTWGQRI
Ssp 361   EFGDQHSDGNPDEDAIMATAQSLRIGYLGWSWSGNGSGVEYLDMVNGFDPCSLTNWGNRF
Sco 260   EFGDQHSDGNPDEDAIMATAQSLGVGYLGWSWSGNGGGVEYLDMVNGFDPNSLTSWGNRI
Sli 277   EFGDQHSDGNPDEDAIMATAQSLGVGYLGWSWSGNGGGVEYLDMVNGFDPNSLTSWGNRI
              *                                          *
Csp 308   VHGAIGERARNAPAASVYGGLGGDGDGGAG--------TAPNGYDYCASASS-DPDGDGW
Msp 311   INGANGIKATSKEASVYGGIVTPTPSTTVTPTLPPPTTTPPPTTPPATGGCT-ATYTIVG
Ssp 421   FNGSNGIAATSERATVYGSGLGGDG-----------GTAPNGYPYCVNESSSDPDGDGR    CBM 10
Sco 320   FYGSNGIAATSRTATVYGGGGG--------------------------------
Sli 337   LYGSNGIAATSRTATVYGGGGG--------------------------------

Csp 359   GWESSASCVRGSSADTGSGGGSSGSTAPNGYPYCASASSDPDGDGWGWESSASCVVRG
Msp 370   CWQGGFQGEVRVTAGSAAINGWTAKWTYPGQISCVRNATVTSSGSSVTAINVSYNGHLG
Ssp 470   GWENNRSCVRGSSADTGS---SLGGTAPNGYPYCVNGSSSDPDGDGWGWENNRSCVVRG    CBM 10
Sco 342   -------------------STGGTAPNGYPYCVNGCASDPDGDGWGWENSRSCVVRG
Sli 359   -------------------STGGTAPNGYPYCVNGCASDPDGDGWGWENSRSCVVRG

Csp 419   SSADR-----------------------
Msp 430   TCASTSFGFIGSSTGTPTVPAVTCTAS
Ssp 527   SSADH-----------------------
Sco 380   SAADH-----------------------
Sli 397   SAADH-----------------------
```

MANNANASE PRODUCED FROM CELLULOSIMICROBIUM SP. STRAIN HY-13

This patent application is the National Stage of International Application No. PCT/KR2011/010245 filed Dec. 28, 2011, which claims the benefit of priority from Korean Application No. 10-2011-0070462, filed Jul. 15, 2011, each of which are herein incorporated by reference in their entirety.

BACKGROUND OF THE INVENTION

1. Field of the Invention

The present invention relates to a novel mannanase produced from *Celluosimicrobium* sp. strain HY-13

2. Description of the Related Art

Cellulose and hemicellulose decomposing microorganisms are found in soil and compost related ecosystem, and digestive canals of herbivores and invertebrates. These microorganisms play an important role in biological transformation of biomass (Flint et al., 2008, Nat. Rev. Microbiol. 6, 121-131; Kim et al., 2009, Appl. Environ. Microbiol. 75, 7275-7279; Perez et al., 2002, Int. Microbiol. 5, 53-63).

Among structural polysaccharides found in plant biomass, β-1,4-mannan is the hemicellulose of softwood and is often found in various lignocellulose biomasses as heteropolysaccharide containing glucose and/or galactose units (van Zyl et al., 2010, Proc. Biochem. 45, 1203-1213). During the biodegradation of cellulose and xylan, mannan polysaccharide is also completely degraded by the cooperation of various hydrolases such as β-mannanase, β-mannosidase, β-glucosidase, α-galactosidase, and acetyl mannan esterase, according to the previous reports (Shallom and Shoham, 2003, Curr. Opin. Microbiol. 6, 219-228; Walker and Wilson, 1991. Bioresour. Technol. 36, 3-14).

β-1,4-mannanase is the endo-enzyme that degrades β-1,4-mannosidic binding in mannan polysaccharides randomly. Such glycoside hydrolase (GH) has the typical molecular structure composed of $(\beta/\alpha)_8$-barrel exhibiting double confront mechanism having anomer structure (Moreira and Filho, 2008, Appl. Microbiol. Biotechnol. 79, 165-178). β-1,4-mannanase in microorganism seems to be related to three GH family members, 5, 26, and 113, based on the amino acid sequence and structural/mechanical homology (cazy with the extension .org of the world wide web). Approximately 140 gene sequences of β-1,4-mannanase can be obtained from NCBI data-base. The homology among many genes encoding β-1,4-mannanase, which are originated from various bacteria and fungi, has been confirmed by genome analysis. Nevertheless, genetic and biochemical characteristics of β-1,4-mannanase originated from microorganism have not been disclosed as much as the characteristics of β-1,4-endoglucanases and β-1,4-xylanases.

Various aerobic and anaerobic cellulose decomposing microorganisms found in intestines of invertebrates and herbivores drew our attention recently as promising candidates capable of producing a novel GH enzyme having specific structural and functional characteristics (Brennan et al., 2004, Appl. Environ. Microbiol. 70, 3609-3617; Selinger et al., 1996, Anaerobe 2, 263-284). Even though it is presumed that an invertebrate such as earthworm that magnetizes soil organic matters has various cellulose decomposing microorganisms, most carbohydrolases have been confirmed to be the enzymes that degrade cellulose and xylan originated from rumen bacteria and insect intestine bacteria.

Two hemicellulose decomposing bacteria identified so far are *Cellulosimicrobium* sp. HY-13 (Kim et al., 2009, Proc. Biochem. 44, 1055-1059; Kim et al., 2009, Appl. Environ. Microbiol. 75, 7275-7279) and *Streptomyces thermocarboxydus* HY-15 (Kim et al., 2010, J. Mol. Catal. B: Enzym. 62, 32-39), which have been isolated from *Eisenia fetida* intestines. Extracellular endo-β-1,4-xylanase thereof was identified and molecularly confirmed. However, there have been no studies to disclose the characteristics of mannanase produced from the earthworm symbiotic microorganism at molecular level.

Thus, the present inventors identified the novel mannanase originated from *Celluosimicrobium* sp. strain HY-13, the earthworm symbiotic bacterium, and further disclosed the structural and biochemical characteristics of the mannanase along with the optimum conditions for the specific activity. The present inventors thereby completed this invention by confirming that GH5 β-1,4-mannanase identified to have high specific activity toward ivory nut mannan and locust bean gum could be effectively used as a feed efficiency enhancer.

SUMMARY OF THE INVENTION

It is an object of the present invention to provide a novel mannanase produced from *Cellulosimicrobium* sp. HY-13.

To achieve the above object, the present invention provides a novel mannanase produced from *Cellulosimicrobium* sp. HY-13 deposited under the Accession Number of KCTC 11302BP.

The present invention also provides a polynucleotide encoding the said mannanase.

The present invention further provides a vector containing the said polynucleotide.

The present invention also provides a transformant constructed by transforming the host cell with the said vector.

The present invention also provides a method for producing a mannanase by culturing the said strain.

The present invention also provides a feed additive containing the said mannanase as an active ingredient.

The present invention also provides a plant feed containing the said feed additive as an active ingredient.

The present invention also provides a use of the said mannanase, the said transformant, or the said mannanase produced by the said method for the preparation of a feed additive.

In addition, the present invention also provides a use of the said feed additive for the preparation of a plant feed.

Advantageous Effect

As explained hereinbefore, the present invention provides a gene sequence and an amino acid sequence of a novel mannanase produced from *Cellulosimicrobium* sp. HY-13 and also provides information on substrate specificity and characteristics of the mannanase. The mannanase of the present invention can be efficiently, industrially used for biomass and feedstuffs to degrade hemicellulose included in grains and plants.

BRIEF DESCRIPTION OF THE DRAWINGS

The application of the preferred embodiments of the present invention is best understood with reference to the accompanying drawings, wherein:

FIG. 2 is a diagram illustrating the result of gene sequencing of the mannanase isolated from *Cellulosimicrobium* sp. HY-13.

FIG. 3 is a diagram illustrating the result of investigation of homology and classification at molecular level by analyzing amino acid sequence of the mannanase of the present invention:

Csp: *Cellulosimicrobium* sp. HY-13 mannanase;
Msp: *Micromonospora* sp. β-1,4-mannosidase (GenBank Accession Number: GG657738);
Ssp: *Streptomyces* sp. s6-204 β-1,4-mannanase (ABY90130);
Sco: *S. coelicolor* A3 β-1,4-mannosidase (CAA20610); and
Sli: *S. lividans* TK24 β-1,4-mannanase (EFD65759).

Lane S: standard marker protein;
Lane 1: soluble cell lysate obtained after IPTG (isopropyl-β-D-thiogalactoside) induction;
Lane 2: protein concentrated after affinity chromatography;
Lane 3: protein concentrated after gel permeation chromatography;
Lane 4: protein after anion exchange chromatography; and
Lane 5: active staining of protein obtained by affinity chromatography (Congo red staining).

DESCRIPTION OF THE PREFERRED EMBODIMENTS

Hereinafter, the present invention is described in detail.

The present invention provides a mannanase produced from *Cellulosimicrobium* sp. HY-13 deposited under the Accession Number of KCTC 11302BP.

The said mannanase characteristically has the amino acid sequence represented by SEQ. ID. NO: 1, but not always limited thereto.

Molecular weight of the said mannanase is characteristically 43.0~45.0 kDa, but not always limited thereto.

The said mannanase preferably shows the maximum activity at pH 5.0~7.0, and more preferably shows the maximum activity at pH 6.0, but not always limited thereto.

The said mannanase preferably shows the maximum activity at 45~55° C., and more preferably shows the maximum activity at 50° C., but not always limited thereto.

The said mannanase characteristically exhibits the stable enzyme activity in the presence of one of metal ions selected from the group consisting of Ca, Ni, Cu, Zn, Mg, Mn, Sn, Ba, Co, and Fe, but not always limited thereto.

The said mannanase exhibits the increased enzyme activity in the presence of one of metal ions selected from the group consisting of Ca, Mn, and Ba, but not always limited thereto.

The said mannanase demonstrates the high activity toward such matrix as locust bean gum and ivory nut, but not always limited to those matrixes.

The said mannanase exhibits the endo-β-1,4-mannanase activity, but not always limited thereto.

In a preferred embodiment of the present invention, the present inventors obtained the strain demonstrating mannanase activity, among earthworm enteric bacteria, cultured on LB agar medium containing Azo-mannan. Since the strain had at least 99.8% homology with *Cellulosimicrobium funkei* ATCC BAA-886, the strain of the present invention was identified as *Cellulosimicrobium* sp. strain and then named *Cellulosimicrobium* sp. HY-13 (see FIG. 1). The strain was deposited at Korean Collection for Type Cultures, Korea Research Institute of Bioscience and Biotechnology, one of international depository authorities, in Mar. 12, 2008 (Accession No: KCTC 11302BP).

Chromosome DNA was extracted from *Cellulosimicrobium* sp. HY-13, which proceeded to PCR with the gene sequence common to GH5 endo-β-1,4-mannanase. Total mannanase gene sequence was obtained by cloning the PCR product into pGEM-T vector (Promega). The mannanase gene and other mannanase like enzyme analogues proceeded to multiple sequence alignment. As a result, the mannanase was confirmed to be very similar to extracellular GH5 endo-β-1,4-mannanase, suggesting that the mannanase has the molecular structure of endo-β-1,4-mannanase (see FIG. 2). Sequence homology of mannanase catalytic GH5 domain and extracellular GH5 mannanase was very low. The mannanase exhibited highest homology with *Micromonospora* sp. β-1,4-mannosidase (GenBank Accession Number: GG657738), which was 65%, indicating that the mannanase of the present invention was the novel enzyme (see FIG. 3).

Sequence confirmed mannanase gene was expressed and the enzyme was isolated and purified therefrom. To examine the molecular weight of the purified enzyme, SDS-PAGE was performed. As a result, it was confirmed that the mannanase protein was the enzyme having the molecular weight of approximately 44 kDa.

Figure 5:
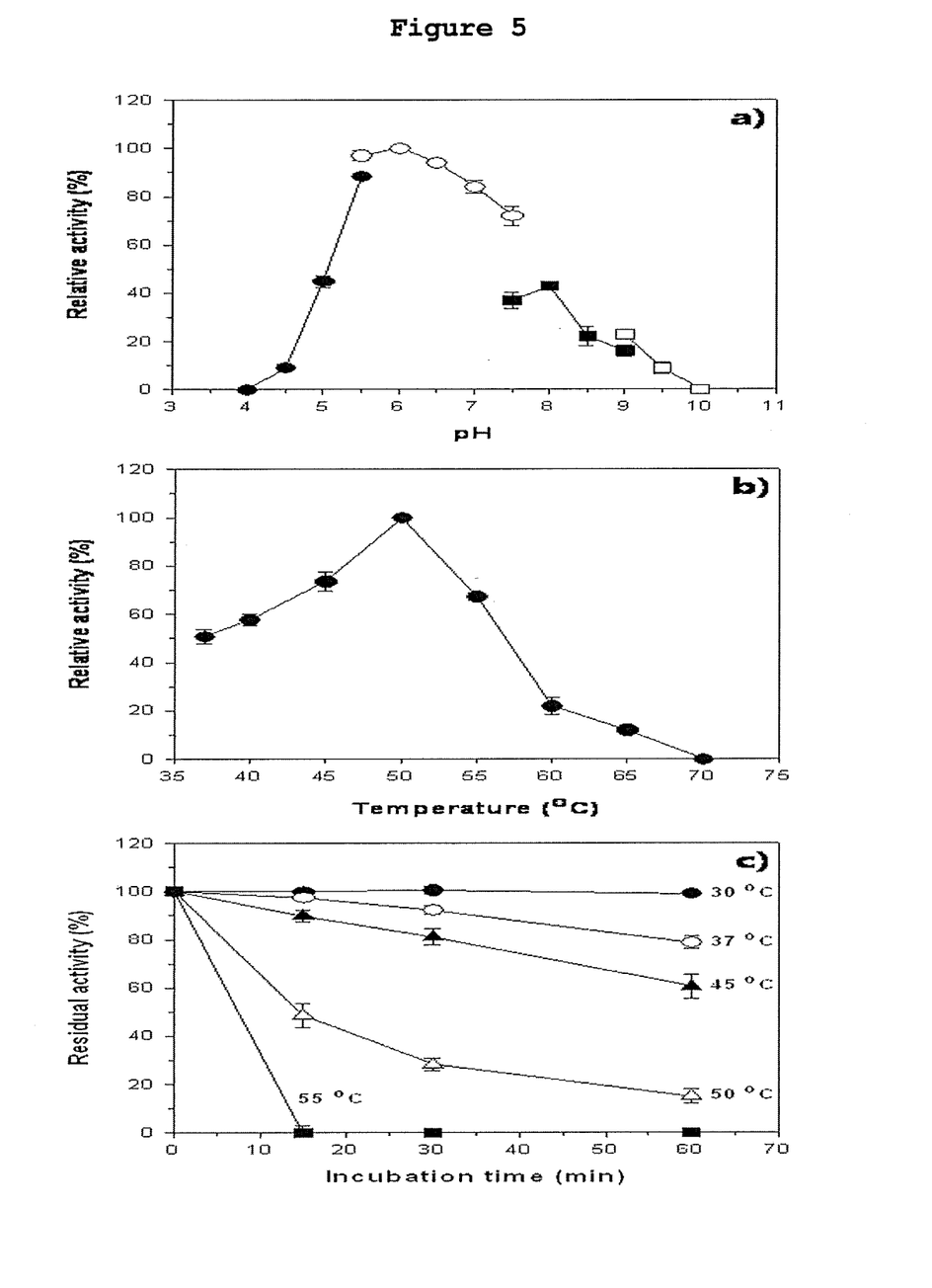
FIG. 5 is a diagram illustrating the result of investigation of optimum reaction temperature, pH, and stability of the purified mannanase of the present invention.

To investigate the characteristics of the mannanase, the optimum reaction temperature was examined at different temperatures of 37, 40, 45, 50, 55, 60, 65, and 70° C. The optimum reaction pH was also examined at pH 4.0~10.0. Particularly, the maximum degrading activity of the mannanase to the matrix was confirmed when the mannanase was reacted with locust bean gum at 50° C. at pH 6.0 (see FIGS. 5a and 5b). Half life of the enzyme was confirmed as 15 minutes at the optimum temperature (50° C.), which would be the thermolabile index of the mannanase. Thermolability of the mannanase was rapidly increased when the mannanase was exposed on the temperature of 55° C.

To investigate the effect of metal ions and chemicals on mannanase activity, metal ions (1 mM) and chemicals (5 mM) were treated to mannanase in 50 mM sodium phosphate buffer (pH 6.0) at 50° C. for 10 minutes, followed by investigation of mannanase activity. As a result, catalytic activity of the mannanase was approximately at least 1.4 fold increased in the presence of $Ca^{2+}$. In the meantime, the mannanase activity was approximately 1.2 fold increased in the presence of divalent cations such as $Mn^{2+}$ and $Ba^{2+}$ (see Table 1).

Therefore, the novel enzyme produced from *Cellulosimicrobium* sp. HY-13 can be effectively used as a mannanase.

The present invention also provides a polynucleotide encoding the said mannanase.

The said polynucleotide is preferably encoding the sequence represented by SEQ. ID. NO: 2, but not always limited thereto.

The present invention further provides a vector containing the said polynucleotide.

The present invention also provides a transformant constructed by transforming the host cell with the said vector.

In this invention, the novel mannanase originated from *Celluosimicrobium* sp. strain HY-13, the earthworm symbiotic bacterium, was identified. The structural and biochemical characteristics of the mannanase were confirmed along with the optimum conditions for the specific activity. Particularly, the mannanase was identified as GH5 β-1,4-mannanase exhibiting the high specific activity toward ivory nut mannan and locust bean gum. Therefore, the polynucleotide encoding the said mannanase, the vector comprising the same, and the transformant of the vector can be effectively used.

The present invention also provides a method for producing a mannanase comprising the following steps:

1) culturing *Celluosimicrobium* sp. strain HY-13 deposited under the Accession Number of KCTC 11302BP in the medium containing mannan, and obtaining supernatant by centrifuging thereof;

2) inducing precipitation of water-soluble proteins by adding a precipitant to the supernatant of step 1);

3) obtaining a crude enzyme solution by dialyzing the precipitate of step 2) after eliminating insoluble precipitate from the same; and 4) purifying mannanase from the crude enzyme solution of step 3).

The precipitant of step 2) is preferably selected from the group consisting of ammonium sulfate, acetone, isopropanol, methanol, ethanol, and polyethyleneglycol, but not always limited thereto.

In a preferred embodiment of the present invention, centrifugation was performed to isolate cells from the culture solution. The isolated cells were treated with a protein separation solution (Novagen), which proceeded to centrifugation to obtain a crude enzyme solution. The crude enzyme solution obtained via centrifugation was loaded on HisTrap HP affinity column chromatography, leading to enzyme elution. The eluted fraction was loaded on HiPrep 26/10 desalting column to eliminate salts. The desalted fraction was loaded on Hiload 26/60 Superdex 200 equilibrated with 20 mM Tris-HCl buffer (pH 7.6). For further purification, the obtained active fraction was loaded on Hiprep 16/10 DEAE FF anion-exchange column chromatography. As a result, the mannanase purified under the conditions of 1.0 M NaCl and 2.0 Ml/min was obtained.

The mannanase obtained by the above production method was identified as GH-5 β-1,4-mannanase demonstrating high substrate specificity to mannan. Therefore, the said method can be effectively used for the production of the novel mannanase from *Celluosimicrobium* sp. strain HY-13.

The present invention also provides a feed additive containing the said mannanase as an active ingredient.

The feed additive herein is added to non-ruminant feed, but not always limited thereto.

The present invention also provides a plant feed containing the said feed additive as an active ingredient.

The present invention also provides a use of the said mannanase, the said transformant, or the said mannanase produced by the said method for the preparation of a feed additive.

In addition, the present invention also provides a use of the said feed additive for the preparation of a plant feed.

In a preferred embodiment of the present invention, mannanase activity against various matrixes was compared. Particularly, locust bean gum, ivory nut mannan, and guar gum were used as different matrixes to compare the enzyme activity of the purified mannanase. As a result, the mannanase of the present invention was confirmed to be the enzyme having high activity of 14,711 IU/mg to ivory nut mannan. The enzyme activity to locust bean gum and guar gum of the said mannanase of the present invention was respectively 8,498 IU/mg and 967 IU/mg. Carbohydrates such as carboxymethylcellulose, Birchwood xylan, soluble starch, and pectin were not degraded by the mannanase. Therefore, it was presumed that the mannanase was the strict GH5 β-1,4-mannanase lacking of glycoside hydrolase activity. The mannanase of the present invention was therefore confirmed to be able to degrade mannan efficiently and specifically and further to be efficiently used for animal feed considering that most of recent plant feeds for animal contain a high concentration of mannan. As explained hereinbefore, the mannanase of the present invention is suitable as a feed additive designed to be enhance mannan degrading activity in plant feed, suggesting that the mannanase of the invention can be effectively used as a feed additive for mannan glycation.

When the feed additive of the present invention is added to those feeds for non-ruminant such as pig and chicken which exhibit low efficiency in using starch or protein in grain cell wall because the feeds do not include the enzyme degrading plant cell wall, the additive can glycosylate mannan, the major component of cell wall, to bring the effect of increasing feed value.

As an active ingredient, the mannanase of the present invention is added to feed preferably at the concentration of 0.01~10 weight part and more preferably at the concentration of 0.05~5 weight part, and most preferably at the concentration of 0.12 weight part.

The said feed additive herein can additionally include any acceptable carrier for non-ruminant. In this invention, the feed additive can be used as it is or include any generally informed carrier or stabilizer. If necessary, nutrients such as vitamins, amino acids, and minerals, or antioxidants and other additives can be added to the feed additive of the present invention. The feed additive can be formulated in the forms of powder, granule, pellet, and suspension. For the administration, the feed additive of the present invention can be provided to non-ruminant singly or as mixed in feed.

The present inventors identified the novel mannanase produced from *Celluosimicrobium* sp. strain HY-13, the earthworm symbiotic bacterium. The structural and biochemical characteristics of the mannanase were confirmed along with the optimum conditions for the specific activity. Particularly, the mannanase was identified as GH5 β-1,4-mannanase exhibiting the high specific activity toward ivory nut mannan and locust bean gum. Therefore, the present invention can provide a feed additive containing the said mannanase as an active ingredient for mannan glycation. The mannanase of the present invention can also be added to feed for non-ruminant or plant feed as an active ingredient to increase mannan glycation.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

Example 1

Identification of *Cellulosimicrobium* sp. HY-13

Figure 1:
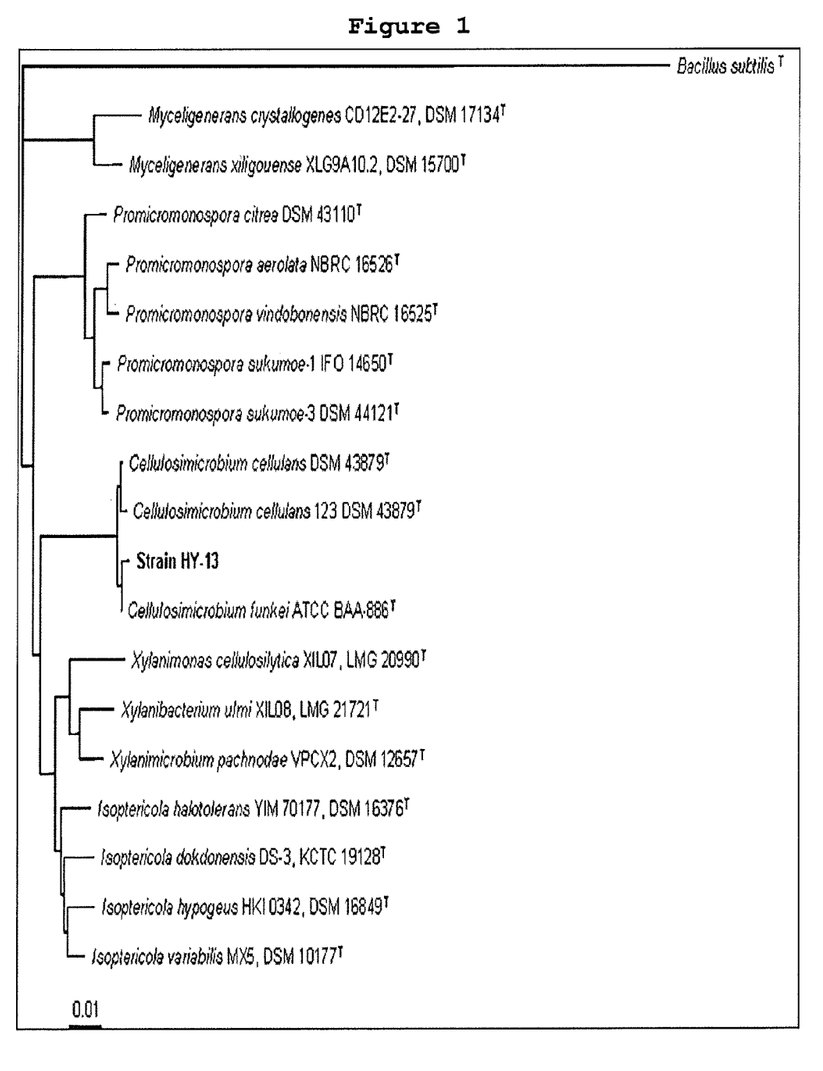
FIG. 1 is a diagram illustrating the identification of 16S rDNA of *Cellulosimicrobium* sp. HY-13 producing the mannanase of the present invention.

Among earthworm enterobacteria, microflora of the strain showing mannanase activity was obtained on LB agar medium containing Azo-mannan. Characteristics of the strain producing the mannanase showing the highest activity was analyzed. To identify the separated strain, 16s rDNA sequencing was performed. As a result, the strain was confirmed to have at least 99.8% homology with *Cellulosimicrobium funkei* ATCC BAA-886, so that the strain was identified as *Celluosimicrobium* sp. and named *Celluosimicrobium* sp. HY-13 (FIG. 1). The *Celluosimicrobium* sp. strain HY-13 demonstrating the highest mannanase activity separated above was stored in a freezer and deposited at Korean Collection for Type Cultures, Korea Research Institute of Bioscience and Biotechnology (Accession No: KCTC 11302BP).

Example 2

Obtaining Mannanase Gene from *Celluosimicrobium* sp. HY-13

<2-1> Separation of Mannanase Gene

Chromosome DNA was extracted from *Cellulosimicrobium* sp. HY-13. Based on the common gene sequences with GH5 endo-β-1,4-mannanase (VDAPNW; SEQ. ID. NO: 3, and GWSWSGN; SEQ. ID. NO: 4), a forward primer (5'-GTCGACGCSCCGAACTGG-3'; SEQ. ID. NO: 5) and a reverse primer (5'-GTTGCCCGACCACGACCAGC-3'; SEQ. ID. NO: 6) were designed as DNA primers for PCR. 50 μl of PCR mixture was prepared with the primers, 2.5 unit polymerase (FastStart Taq DNA polymerase), 2.5 mM of each dNTP, 20 pmol primer, 50 ng of DNA, and buffer. PCR was performed as follows; predenaturation at 95° C. for 5 minutes, denaturation at 95° C. for 30 seconds, annealing at 59° C. for 30 seconds, extension at 72° C. for 3 minutes 35 cycles from denaturation to extension, and final extension at 72° C. for 30 seconds. The PCR product was cloned in pGEM-T vector (Promega), from which total mannanase gene sequence was obtained (FIG. 2).

<2-2> Characteristics of Mannanase Gene

Multiple sequence alignment was performed with the said mannanase gene and other similar enzyme sequences. As a result, the said mannanase was confirmed to be very similar to extracellular GH5 endo-β-1,4-mannanase, suggesting that the said mannanase had the molecular structure similar to that of the endo-β-1,4-mannanase (FIG. 2). The said mannanase was also confirmed to be the multi-domain protein having a GH5 catalytic domain and two CBM like domains on C-terminal.

Sequence homology was compared between catalytic GH5 domain of the mannanase and extracellular GH5 mannanase, and as a result, the sequence homology was comparatively low. The highest sequence homology was confirmed between the said domain and *Micromonospora* sp. β-1,4-mannosidase (GenBank Accession Number: GG657738), which was 65%. The homology between the mannanase and *Streptomyces* sp. s6-204 β-1,4-mannanase (ABY90130) and the homology between the mannanase and *S. coelicolor* A3 β-1,4-mannosidase (CAA20610) were also 62%. S. The sequence homology between the mannanase and *S. lividans* TK24 β-1,4-mannanase (EFD65759) was 61%. Therefore, the mannanase of the present invention was confirmed to be the novel enzyme (FIG. 3).

Example 3

Expression, Purification, and Analysis of Mannanase

<3-1> Expression and Purification of Mannanase

To express the mannanase gene whose gene sequence was already identified and to separate and purify the enzyme, the expression vector pET-28a(+) was digested with NdeI/HindIII. The pGEM-T vector containing the recombinated mannanase gene of Example 2 proceeded to PCR using DNA primers containing NdeI/HindIII restriction enzyme sites respectively in N-terminal and C-terminal. As a result, DNA fragment was obtained. *E. coli* BL21 was transformed with the pGEM-T(+) expression vector containing the recombinated mannanase gene. From the transformant, colonies were obtained. Particularly, the transformed strain was cultured in 2 l baffled-flask containing 500 Ml of Luria-Bertani medium at 30° C. at 180 rpm for 7 hours. To induce over-expression of the mannanase, 1 mM of IPTG (isopropyl-β-D-thiogalactoside) was added to the medium. When absorbance (A600) of the culture solution reached 0.4~0.5, the medium was centrifuged at 7000 rpm for 20 minutes. The supernatant was discarded and the precipitate (cells) was stored at −20° C. for 1 hour. The separated cells were treated with BugBuster protein isolation solution (Novagen), followed by centrifugation at 12,000 rpm for 20 minutes to obtain a crude enzyme solution. The obtained crude enzyme solution proceeded to HisTrap HP affinity column chromatography and the recombinated enzyme was eluted by the manufacturer's protocol. Salt was eliminated from the obtained active fraction by loading the fraction on HiPrep 26/10 desalting column in 20 mM Tris-HCl buffer (pH 7.6). The desalted fraction was loaded on Hiload 26/60 Superdex 200 equilibrated with 20 mM Tris-HCl buffer (pH 7.6). For further purification, the obtained active fraction was loaded on Hiprep 16/10 DEAF FF anion-exchange column chromatography. As a result, a mannanase purified under the conditions of 1.0 M NaCl and 2.0 Ml/min was obtained.

<3-2> Analysis of Mannanase

SDS-PAGE (sulfate-polyacrylamide gel electrophoresis) was performed on 12.0% gel, followed by staining with Coomassie brilliant blue R-250. Then, zymography analysis was performed with the recombinated protein purified by affinity chromatography on 12.0% polyacrylamide gel containing 0.5% locust bean gum. After SDS-PAGE, bio-degradation was induced for 15 minutes at 50° C. Upon completion of the reaction, β-1,4-mannanase activity was investigated by Congo red staining.

Figure 4:
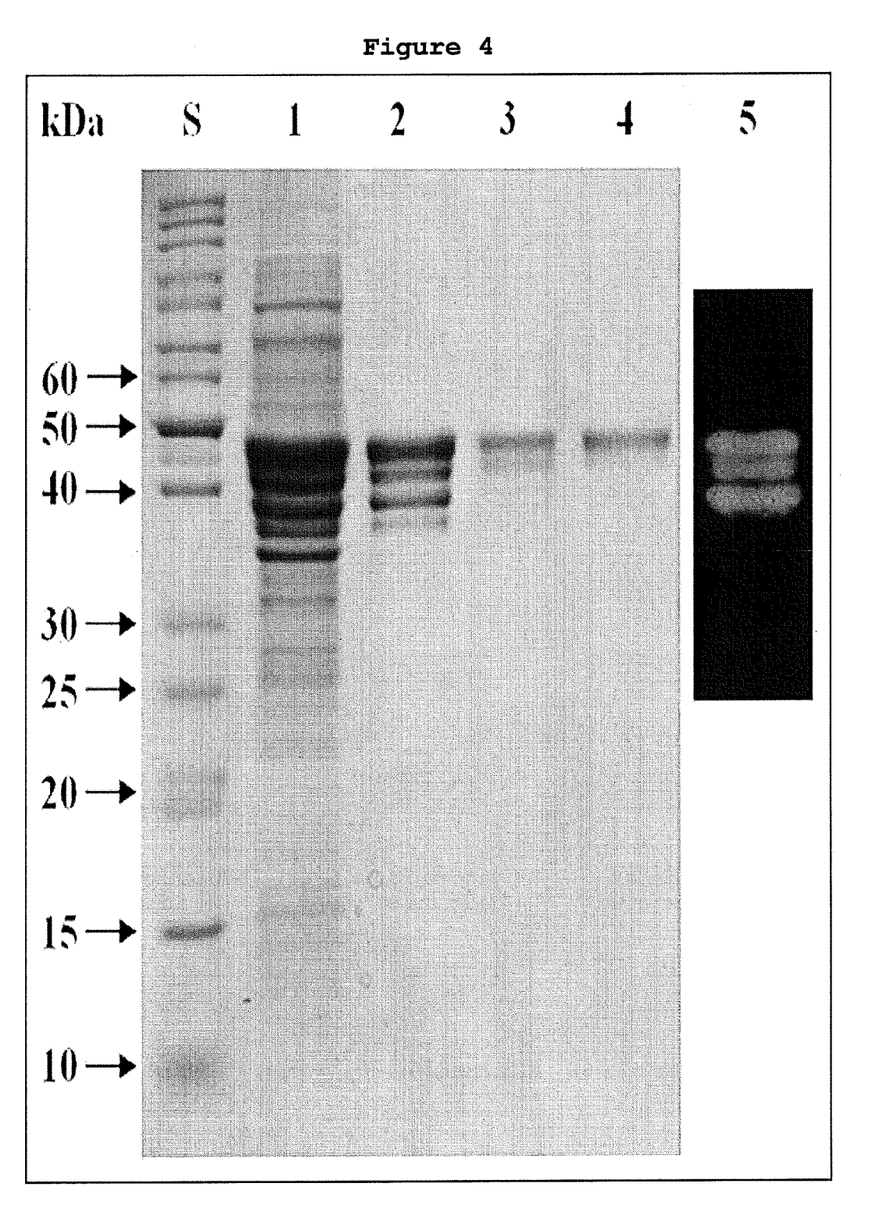
FIG. 4 is a diagram illustrating the result of molecular weight analysis with the purified mannanase by 12.0% SDS-PAGE electrophoresis and the result of zymography.

As a result, the mannanase was confirmed to be the enzyme having the molecular weight of approximately 44 kDa. Compared with the β-1,4-mannanase reported previously, the recombinated mannanase of the present invention had the molecular weight most similar to that of *Aspergillus aculeatus* endo-β-1,4-mannanase. The molecular weight of the recombinated mannanase was bigger than those of *Cellulosimicrobium* sp. HY-13 Mank (35.0 kDa) and *S. lividans* 66 β-mannanase (36.0 kDa) (FIG. 4). However, the molecular weight of the said mannanase was smaller than that of non-multifunctional GH-5 (β-mannanase (>60.0 kDa) known to have relative high molecular weight (FIG. 4).

Example 4

Characteristics of Mannanase

<4-1> Optimum Temperature, pH, and Chemical Properties of Mannanase

To determine the optimum reaction temperature of the mannanase, mannanase activity was measured at different temperatures of 37, 40, 45, 50, 55, 60, 65, and 70° C. To measure thermo-stability, the mannanase was heat-treated at the said temperatures for 15, 30, and 60 minutes and then the remained activity was measured. To determine the optimum reaction pH, the mannanase was treated respectively with 50 mM of sodium citrate buffer (pH 4.0~5.5), phosphate buffer (pH 5.5~7.5), Tris-HCl buffer (pH 7.5~9.0), and glycine-NaOH buffer (pH 9.0~10.0) in pH range of 4.0~10.0 at 55° C. for 15 minutes, followed by measurement of enzyme reaction.

As a result, the maximum degrading activity of the mannanase to the matrix was confirmed when the mannanase was reacted with locust bean gum at 50° C. at pH 6.0 (FIGS. 5a and 5b). Half life of the enzyme was confirmed as 15 minutes at the optimum temperature (50° C.), which would be the thermolabile index of the mannanase. Thermolability of the mannanase was rapidly increased when the mannanase was exposed on the temperature of 55° C. (FIG. 5c).

<4-2> Effect of Metal Ions and Chemicals on Mannanase Activity

To investigate the effect of metal ions and chemicals on mannanase activity, metal ions (1 mM) and chemicals (5 mM) were treated to mannanase in 50 mM sodium phosphate buffer (pH 6.0) at 50° C. for 10 minutes, followed by investigation of mannanase activity.

As a result, catalytic activity of the mannanase was approximately at least 1.4 fold increased in the presence of $Ca^{2+}$. In the meantime, the mannanase activity was approximately 1.2 fold increased in the presence of divalent cations such as $Mn^{2+}$ and $Ba^{2+}$. However, $Mg^{2+}$ or $Sn^{2+}$ had no effect on the enzyme activity. In the meantime, the powerful Trp regulators such as $Hg^{2+}$ and N-bromosuccinimide inactivated the mannanase, and such metal ions as $Cu^{2+}$, $Zn^{2+}$ and $Fe^{2+}$ inhibited the enzyme activity significantly at least 50% (Table 1).

TABLE 1

| Compound | Relative activity (%) |
| --- | --- |
| None | 100.0 |
| $HgCl_2$ | 0 |
| $CaCl_2$ | 146.9 |
| $NiSO_4$ | 67.1 |
| $CuCl_2$ | 16.7 |
| $ZnSO_4$ | 47.4 |
| $MgSO_4$ | 99.9 |
| $MnCl_2$ | 125.2 |
| $SnCl_2$ | 103.7 |
| $BaCl_2$ | 118.5 |
| $CoCl_2$ | 111.9 |
| $FeSO_4$ | 42.2 |
| N-Bromosuccinimide | 0 |
| Odoacetamide | 113.3 |
| Sodium azide | 145.7 |
| N-Ethylmaleimide | 121.4 |
| EDTA | 19.0 |
| Tween 80 (0.5%) | 103.5 |
| Triton X-100 (0.5%) | 98.9 |

Example 5

Substrate Specificity of Mannanase

To compare the mannanase activity to different matrixes, locust bean gum, ivory nut mannan and guar gum were used as matrixes and the activity of the purified mannanase to those matrixes were investigated.

The activity of β-1,4-mannanase was investigated by measuring the reduced amount of glucose isolated from locust bean gum using 3,5-dinitrosalicylic acid (DNS). At this time, D-mannose was used as a standard material. 0.5 Ml of a standard mixture composed of 0.5% locust bean gum was mixed with 0.05 Ml of an enzyme aqueous solution, followed by inducing biodegradation reaction in 50 mM sodium phosphate buffer (pH 6.0) at 50° C. for 15 minutes. The activity of the recombinated mannanase (1 IU) to the mannan substrate was defined as the amount of the protein necessary for the secretion of 1 μmol reducing sugar under the standard analysis condition. Chromogenic PNP-sugar derivative was used to measure another degrading activity of the said recombinated enzyme. The enzyme activity of the recombinated mannanase to the chromogenic substrate was measured under the same conditions as set for the analysis of β-1,4-mannanase activity. The activity of the recombinated mannanase (1 IU) to the PNP-sugar derivative was defined as the amount of the protein necessary for the production of 1 μmol PNP under the standard analysis condition.

As a result, the mannanase of the present invention was confirmed to be the enzyme having high activity of 14,711 IU/mg to ivory nut mannan. The enzyme activity to locust bean gum and guar gum of the said mannanase of the present invention was respectively 8,498 IU/mg and 967 IU/mg. The above results indicate that the specific activity of the mannanase to ivory nut mannan was 1.7 fold and 15.2 fold higher that the activity to locust bean gum and guar gum (Table 2 and Table 3). In the meantime, carbohydrates such as carboxymethylcellulose, Birchwood xylan, soluble starch, and pectin were not degraded by the mannanase. Therefore, it was confirmed that the mannanase was the strict GH5 β-1,4-mannanase lacking of glycoside hydrolase activity (Table 3).

TABLE 2

| Strain | Enzyme | M.W. (kDa) | Opt. pH | Opt. temp. (° C.) | Specific activity (IU/mg) |
| --- | --- | --- | --- | --- | --- |
| Cellulosimicrobium sp. HY-13 | rManH[a] | 44.0 | 6.0 | 50 | 14,711[c] |
| Cellulosimicrobium sp. HY-13 | rManH[a] | 44.0 | 6.0 | 50 | 8,498[d] |
| Streptomyces sp. S27 | Man5S27[a] | 43.0 | 7.0 | 65 | 2,107[d] |
| Bacillus circulans CGMCC1554 | Man5A[a] | 32.0 | 7.6 | 60 | 4,839[d] |
| Bacillus subtilis WY34 | Mannanase[b] | 39.6 | 6.0 | 65 | 8,302[d] |

[a]Recombinant GH5 β-1,4-mannanase produced in E. coli.
[b]Wild type β-1,4-mannanase.
[c]Specific activity toward insoluble ivory nut mannan.
[d]Specific activity toward locust bean gum.

TABLE 3

| Substrate | Specific activity (IU mg$^{-1}$)[a] |
| --- | --- |
| Locust bean gum | 8,498 ± 105 |
| Guar gum | 967 ± 18 |
| Insoluble ivory nut mannan | 14,711 ± 183 |
| Pectin | ND[b] |
| Birchwood xylan | ND |
| Soluble starch | ND |
| Carboxymethylcellulose | ND |
| PNP-cellobioside | ND |
| PNP-glucopyranoside | ND |
| PNP-xylopyranoside | ND |
| PNP-mannopyranoside | ND |

Example 6

Analysis of Degradation Product

Mannooligomer ($M_2$~$M_5$, 1 mg/100 μl each) and locust bean gum (1.4 mg/100 μl) were reacted in 50 mM sodium phosphate buffer (pH 6.0) containing 1 μg of the recombinant mannanase at 30° C. for 12 hours, followed by investigation of the hydrolysate. HPLC (high performance liquid chromatography) was performed by using Finnigan Surveyor™ Modular HPLC systems (Thermo Electron Co.) equipped with Asahipak NH2P-50 2D column (5 μm, 2.0×150 mm, Shodex) ran by Xcalibur software (version 1.3 SP2, Thermo Electron Co.). Elution buffer A (0.05% pomalus acid/sterilized water) and elution buffer B (acetonitrile and methanol (7:3) containing 0.05% pomalus acid) were used as moving phases. LC-MS/MS (liquid chromatography/tandem mass spectrometry) was performed by using Finnigan LCQ Advantage MAX ion trap mass spectrometer (Thermo Electron Co.).

The mannan hydrolysate produced by the mannanase was investigated by HPLC analysis. As a result, mannan polysaccharide of locust bean gum was primarily degraded into $M_5$ (44.2%) along with mannooligomer (at least $M_6$, 39.4%). And small amount of $M_1$ (1.1%), $M_2$ (6.4%), $M_3$ (1.5%), and $M_4$ (7.4%) were generated as hydrolysates. In the meantime, ivory nut mannan was mostly degraded into $M_4$ (25.2%). Later on, most of $M_3$~$M_5$ were further degraded into $M_2$. $N_2$, as a substrate, was not degraded by the mannanase anymore (Table 4). The above results indicate that the mannanase is the only endo-β-1,4-mannanase able to degrade β-1,4-mannos bond in the major backbone of a mannos material.

TABLE 4

| Substrate | Composition (%) of products formed by hydrolysis reaction | | | | | | | |
|---|---|---|---|---|---|---|---|---|
| | $M_1$ | $M_2$ | $M_3$ | $M_4$ | $M_5$ | $M_6$ | $M_7$ | $M_8$ |
| $M_2$ | | 100.0 | | | | | | |
| $M_3$ | 3.5 | 60.1 | 31.6 | 4.0 | 0.8 | | | |
| $M_4$ | 3.9 | 55.5 | 28.8 | 9.9 | 1.9 | | | |
| $M_5$ | 4.1 | 46.9 | 21.8 | 16.6 | 7.9 | 2.8 | 0.9 | |
| Locust bean gum | 1.1 | 6.4 | 1.5 | 7.4 | 44.2 | 16.1 | 21.4 | 1.9 |
| Ivory nut mannan | 3.3 | 17.5 | 13.9 | 25.2 | 19.7 | 12.9 | 7.5 | 2.9 |

$^a$LC area %

Example 7

Binding Activity of Mannanase to Hydrophobic Polymer

The mannanase of the present invention contains two family 10 CBMs at C-terminal, which plays an important role in enzyme-substrate interaction. As the mannanase was expected to bind to various carbohydrate polymers, hydrophobic materials having microstructures including polysaccharide, poly(3HB) granules, and lignin were used as substrates to investigate enzyme-substrate binding activity of the mannanase.

Before analyzing the binding activity, insoluble substrates were washed with 50 mM sodium phosphate buffer (pH 6.0) 5 times, followed by measuring the binding capacity of the enzyme to the hydrophobic materials. Particularly, the enzyme diluted at the concentration of 5.0 IU/Ml was put on ice for two hours with the equal volume of a substrate polymer. The mixture was stirred every 5 minute. The mixture was centrifuged at 12,000×g to obtain supernatant. Then, the activity of β-1,4-mannanase thereof was measured.

Figure 6:
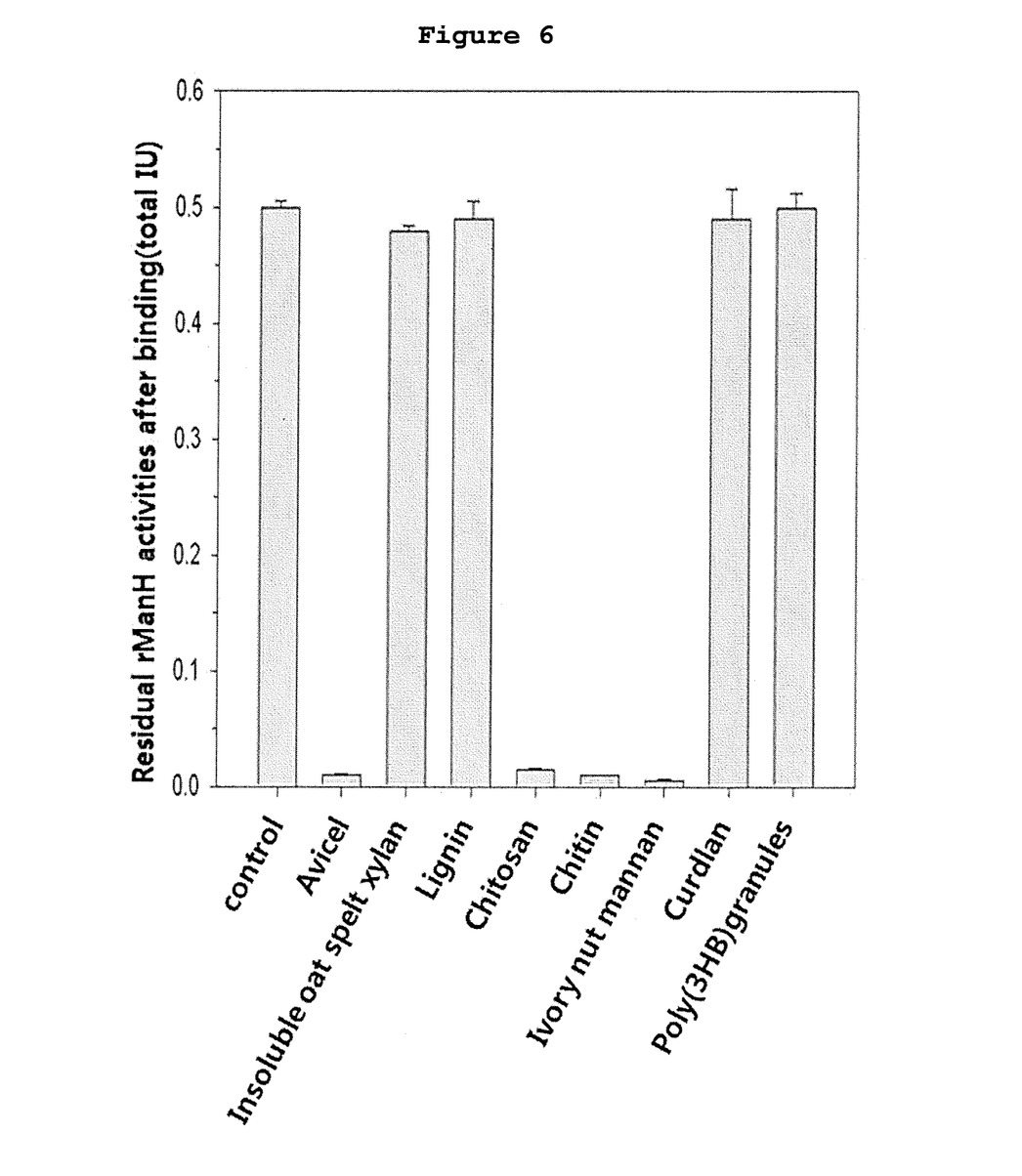
FIG. 6 is a diagram illustrating the binding between the purified mannanase of the present invention and an insoluble polymer.

As a result, the mannanase was strongly conjugated to Avicel, chitosan, chitin, and insoluble ivory nut mannan, but was not conjugated to insoluble oat spelt xylan, lignin, curdlan, and poly(3HB) granules (FIG. 6). Therefore, it was confirmed that the mannanase of the present invention was the novel modular β-1,4-mannanase having affinity to various insoluble polymers.

[Accession Number]

International Depository Authority: Korean Collection for Type Cultures, Korea Research Institute of Bioscience and Biotechnology Accession Number: KCTC11302BP Receipt: 20080312

---

What is claimed is:

1. A method for producing a mannanase comprising the following steps:
   1) culturing *Celluosimicrobium* sp. strain HY-13 deposited under the Accession Number of KCTC 11302BP in a medium containing mannan, and obtaining supernatant by centrifuging thereof;
   2) inducing precipitation of water-soluble proteins by adding a precipitant to the supernatant of step 1);
   3) obtaining a crude enzyme solution by dialyzing the precipitate of step 2) after eliminating insoluble precipitate from the same; and
   4) purifying the mannanase from the crude enzyme solution of step 3).

2. An animal feed comprising grains, plants, and mannan and further comprising the mannanase having the amino acid sequence of SEQ ID NO:1 at a concentration of from 0.05 to about 5 weight part.

3. The animal feed of claim 2 which is a non-ruminant feed.

* * * * *

SEQUENCE LISTING

<160> NUMBER OF SEQ ID NOS: 6

<210> SEQ ID NO 1
<211> LENGTH: 423
<212> TYPE: PRT
<213> ORGANISM: cellulosimicrobium

<400> SEQUENCE: 1

```
Met Arg Arg Leu Phe Ala Ile Val Leu Gly Ala Val Leu Ala Leu Leu
1               5                   10                  15

Ala Val Pro Ala Leu Ala Gln Gly Ala Ser Val Ala Ser Asp Gly Phe
            20                  25                  30

Ser Val Gln Asp Gly Arg Ile Tyr Asp Ala Asn Gly Asn Arg Phe Val
        35                  40                  45

Pro Val Gly Val Asn His Ala His Ala Trp Tyr Pro Ser Gln Thr Gln
    50                  55                  60

Ser Phe Ala Asp Ile Arg Ala Ala Gly Ala Asn Thr Val Arg Val Val
65                  70                  75                  80

Leu Ser Gly Gly Arg Tyr Gly Thr Ser Ser Ala Ala Asp Val Ser Ala
                85                  90                  95

Val Val Glu Arg Cys Lys Gln Asn Gln Leu Val Cys Ile Leu Glu Asn
                100                 105                 110

His Asp Thr Thr Gly Tyr Gly Glu Asp Gly Ser Ala Arg Ser Leu Ala
            115                 120                 125
```

```
Ser Ala Ala Gln Tyr Trp Thr Ser Ile Ala Ser Val Leu Arg Gly Gln
            130                 135                 140

Glu Arg Tyr Val Met Ile Asn Ile Gly Asn Glu Pro Phe Gly Asn Ser
145                 150                 155                 160

Gly Phe Gln Ser Trp Thr Thr Asp Thr Ile Ala Ala Ile Arg Thr Leu
                165                 170                 175

Arg Ala Ala Gly Leu Asp His Thr Leu Val Val Asp Ala Pro Asn Trp
            180                 185                 190

Gly Gln Asp Trp Ser Phe Thr Met Arg Asp Asn Ala Pro Thr Val Ala
        195                 200                 205

Ala Ala Asp Gly Asn Val Val Phe Ser Val His Met Tyr Gly Val Phe
210                 215                 220

Asp Thr Gly Ala Glu Val Arg Ala Tyr Leu Asp Ser Phe Thr Ser Arg
225                 230                 235                 240

Gly Leu Pro Ile Met Val Gly Glu Phe Gly Asp Asn His Ser Asp Gly
                245                 250                 255

Asn Pro Asp Glu Ala Thr Ile Met Ser Tyr Thr Arg Ser Gln Gly Ile
            260                 265                 270

Gly Met Leu Gly Trp Ser Trp Ser Gly Asn Gly Gly Val Glu Tyr
        275                 280                 285

Leu Asp Met Val Asn Gly Phe Ser Ala Ser Ser Leu Thr Pro Trp Gly
        290                 295                 300

Gln Arg Phe Val His Gly Ala Asp Gly Leu Arg Ala Arg Asn Ala Pro
305                 310                 315                 320

Ala Ala Ser Val Tyr Gly Asp Gly Gly Asp Gly Asp Gly Ala
                325                 330                 335

Gly Thr Ala Pro Asn Gly Tyr Pro Tyr Cys Ala Ser Ala Ser Ser Asp
            340                 345                 350

Pro Asp Gly Asp Gly Trp Gly Trp Glu Ser Ser Ala Ser Cys Val Val
        355                 360                 365

Arg Gly Ser Ser Ala Asp Thr Gly Ser Gly Gly Ser Gly Ser Gly
        370                 375                 380

Ser Thr Ala Pro Asn Gly Tyr Pro Tyr Cys Ala Ser Ala Ser Ser Asp
385                 390                 395                 400

Pro Asp Gly Asp Gly Trp Gly Trp Glu Ser Ser Ala Ser Cys Val Val
                405                 410                 415

Arg Gly Ser Ser Ala Asp Arg
            420

<210> SEQ ID NO 2
<211> LENGTH: 1272
<212> TYPE: DNA
<213> ORGANISM: cellulosimicrobium

<400> SEQUENCE: 2
atgagacgac tgttcgccat cgtcctgggc gcggtgctcg ccttgctcgc cgtgccggcg     60
ctcgcgcagg gggcgagcgt cgcgagcgac gggttctccg tccaggacgg gaggatctac    120
gacgcgaacg gcaaccgctt cgtgccggtc ggcgtcaacc acgcgcacgc ctggtacccg    180
tcgcagacgc agtccttcgc cgacatccgc gccgccggcg cgaacaccgt ccgcgtcgtg    240
ctgtcgggcg ccggtacagg gacgagctcg gggccgacg tgagcgccgt ggtcgagcgc    300
tgcaagcaga accagctcgt gtgcatcctc gagaaccacg acacgacggg ctacggcgag    360
gacggcagcg cccggtcgct cgcgagcgcg gcgcagtact ggaccagcat cgcgtcggtc    420
```

```
ctgcgcggcc aggagcggta cgtgatgatc aacatcggca acgagcccct cggcaactcc    480
ggcttccaga gctggacgac ggacacgatc gcggcgatcc ggaccctgcg cgcggcgggc    540
ctcgaccaca cgctcgtcgt ggacgccccg aactgggac aggactggtc gttcaccatg     600
cgcgacaacg ccccgacggt cgcggccgcg acgggaacg tggtcttctc cgtccacatg     660
tacggcgtct tcgacaccgg ggcggaggtg cgcgcgtacc tcgactcctt cacgagccga    720
gggctgccga tcatggtcgg cgagttcggt gacaaccact cggacgggaa cccggacgag    780
gccacgatca tgagctacac gcggtcgcag gggatcggga tgctcggctg gtcgtggtcc    840
ggcaacgggg gcggcgtcga gtacctggac atggtgaacg ggttctccgc gagctcgctc    900
acgccgtggg ggcagcggtt cgtccacggc gccgacgggc tcagggcccg caacgcgccc    960
gcggcctcgg tgtacggggg cgacggcggc gatggagacg gcggagccgg tacggcaccc   1020
aacgggtacc cgtactgcgc gagcgcgtcg tcggacccgg acggggacgg gtggggctgg   1080
gagagcagcg cgtcgtgcgt ggtgcgcggc tcctccgcgg acacgggttc cggcggtggc   1140
tccgggagcg ggagcacggc accgaacggg tacccgtact gcgcgagcgc gtcgtcggac   1200
ccggacgggg acgggtgggg ctgggagagc agcgcctcgt cgtcgtgcg cggctcgtcc    1260 gccgaccgct ga                                                       1272

<210> SEQ ID NO 3
<211> LENGTH: 6
<212> TYPE: PRT
<213> ORGANISM: cellulosimicrobium

<400> SEQUENCE: 3

Val Asp Ala Pro Asn Trp
1               5

<210> SEQ ID NO 4
<211> LENGTH: 7
<212> TYPE: PRT
<213> ORGANISM: cellulosimicrobium

<400> SEQUENCE: 4

Gly Trp Ser Trp Ser Gly Asn
1               5

<210> SEQ ID NO 5
<211> LENGTH: 18
<212> TYPE: DNA
<213> ORGANISM: Artificial Sequence
<220> FEATURE:
<223> OTHER INFORMATION: forward primer for GH5 endo-beta-1,4-mannanase

<400> SEQUENCE: 5
gtcgacgcsc cgaactgg                                                   18

<210> SEQ ID NO 6
<211> LENGTH: 20
<212> TYPE: DNA
<213> ORGANISM: Artificial Sequence
<220> FEATURE:
<223> OTHER INFORMATION: reverse primer for GH5 endo-beta-1,4-mannanase

<400> SEQUENCE: 6
gttgcccgac cacgaccagc                                                 20
```